United States Patent [19]
Reed, Jr.

[11] 3,968,139
[45] July 6, 1976

[54] NITROGEN- AND FLUORINE-CONTAINING COMPOUNDS
[75] Inventor: Samuel Franklin Reed, Jr., Huntsville, Ala.
[73] Assignee: Rohm and Haas Company, Philadelphia, Pa.
[22] Filed: Oct. 30, 1962
[21] Appl. No.: 235,176

[52] U.S. Cl. .................................. 260/467; 149/42; 149/119
[51] Int. Cl.$^2$ ......................................... G07C 77/02
[58] Field of Search ..................................... 260/467

[56] References Cited
UNITED STATES PATENTS

| | | | |
|---|---|---|---|
| 3,347,903 | 10/1967 | Smiley | 260/467 |
| 3,347,904 | 10/1967 | Smiley | 260/467 |
| 3,366,665 | 1/1968 | Tyler | 260/467 |

*Primary Examiner*—Leland A. Sebastian

EXEMPLARY CLAIM

1. Compounds of the general formula

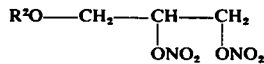

in which $R^2$ is selected from the group consisting of

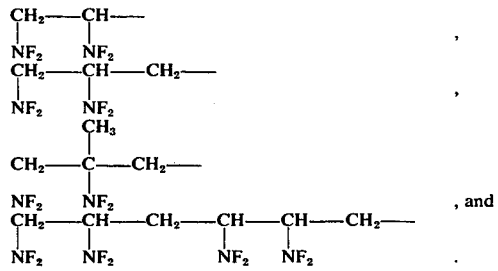
, and 6. A process for the preparation of compounds of the general formula

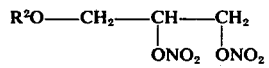

in which $R^2$ is as defined in claim 1, which comprises nitrating, with a mixture of sulfuric and nitric acids, diols of the general formula

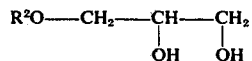

in which $R^2$ is as defined in claim 1.

10 Claims, No Drawings

NITROGEN- AND FLUORINE-CONTAINING COMPOUNDS

This invention concerns high energy compounds which contain nitrogen and fluorine, and which, more specifically, contain $NF_2$ and $ONO_2$ groups.

The compounds of the present invention are of value as plasticizers for nitrocellulose, and are of particular interest because of their high energy characteristics.

The compounds of the present invention are prepared by nitrating bis(difluoramino)-containing glycols with a mixture of nitric and sulfuric acid.

The glycol precursors are prepared by reacting a substituted 1,3-dioxolane with tetrafluorohydrazine, $N_2F_4$. The $N_2F_4$ adds to the double bond, and subsequent hydrolysis of the adduct with dilute acid gives the glycols. The substituted 1,3-dioxolanes are of the general formula

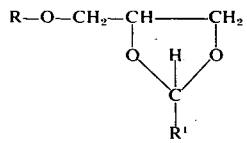

in which
R is $CH_2=CH-$, $CH_2=CH-CH_2-$,

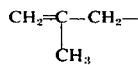

and $CH_2=CH-CH_2-CH=CH-CH_2-$,
$R^1$ and H or lower alkyl C 1 to 4.

Since $R^1$ is removed during hydrolysis and does not appear in the final product, $R^1$ is preferably hydrogen or methyl.

Typical preparations of substituted 1,3-dioxolanes, operable in the present invention, are given in U.S. Pat. No. 2,969,400.

The reaction of $N_2F_4$ with the dioxolane is generally conducted in a solvent, and any solvent which is inert, i.e. does not react with the reactants or the resulting product, is suitable for use. Typical of these are carbon tetrachloride, chloroform, methylene chloride, tetrachloroethane, chlorobenzene, and acetone.

The reaction temperature may be varied from ambient, i.e. 20° to 25° C., to as high as 150° C. However, since the rate of reaction is very slow at low temperatures and proceeds rapidly at high temperatures, it is preferred to use an elevated temperature, preferably in the range 70° to 80° C. One limitation on the use of excessively high temperatures is that the reaction proceeds so violently that it is necessary to use large amounts of solvents to dissipate the heat.

The reaction may be carried out at pressures which range from subatmospheric, for example, 0.5 atm., to 20 to 30 atmospheres.

With the substituted 1,3-oxolanes used as starting materials, one mole of $N_2F_4$ is all that is theoretically required for each double bond. However, an excess of $N_2F_4$ is preferred, since the excess can be easily recovered from the reaction mixture. Since it is preferred that the reaction be conducted at superatmospheric pressure, $N_2F_4$ is fed to the reaction mixture until no further pressure drop occurs.

Typical of the reaction is the reaction of 2-methyl-4-vinoxymethyl-1,3-dioxolane with $N_2F_4$ to give 2-methyl-4-((1,3-bisdifluoramino)ethoxymethyl)-1,3-dioxolane. This product is then hydrolyzed with dilute acid, mineral acids being preferred, HCl being particularly preferred. The bis(difluoramino)dioxolane prepared as described hereinbefore has limited solubilities in dilute acids and it is preferred to add methanol to the solution to increase the solubility of the dioxolane, thus increasing the reaction rate. The preferred ratio of methanol to the aqeuos acid solution is approximately 1:1, but it can be varied widely and still be within the scope of this invention.

The products of the present invention have the following general formula

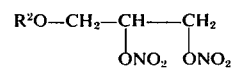

in which $R^2$ is selected from the group consisting of

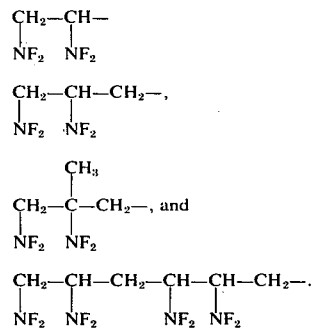

The only pertinent prior art consists of a bis(difluoramino)mononitrate of the following formula:

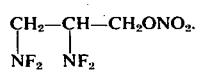

However, this product is of no interest as a plasticizer for compounds like nitrocellulose and other high energy binders, since it fires at two inches, and is too volatile. By contrast, the compound as set forth in claim 2 fires at sixteen to twenty-two inches and, when properly formulated, can show calculated specific impulses (ISE) as high as 275.

Typical propellant formulations are set forth hereinafter.

The products of the present invention are prepared by nitrating the corresponding diol with a mixture of nitric acid and sulfuric acid, the diol being added slowly to the mixed acids. An equimolar mixture of sulfuric and nitric acids represents the preferred proportions. It is preferred to dilute the diol with an inert solvent, such as methylene chloride in order to control better the rate of addition and thus control the exotherm which develops.

It is preferred to maintain the temperature of the mixture at 10° to 25° C. during the addition of the diol, this being done by the application of external cooling means. A reaction temperature of 15° to 20° C. is preferred during the addition, and, when the addition is complete, the mixture is raised to the reflux temperature of the solvent which, in the case of methylene chloride, is 39° to 40° C. The solution is then refluxed for 30 to 90 minutes, cooled and transferred to a separatory funnel. Additional methylene chloride may be added, if required. The acid layer is separated and the solvent solution is washed with water and then with cold saturated sodium carbonate solution to neutralize any residual acid present. After drying in the conventional fashion, the solvent is removed and the product so obtained.

It is preferred to sparge the nitric acid just prior to use so as to remove all the nitrogen oxides frequently present in nitric acid.

The most important use for the products of the present invention is, as previously indicated, in propellant compositions as plasticizers for the propellant grains.

Table I shows typical formulations with the calculated specific impulses of the formulations:

TABLE I

| % NFPA | % NFENG | % APC | % HMX | % AL | ISE |
|---|---|---|---|---|---|
| 15 | 15 | 55 | — | 15 | 267.8 |
| 20 | 20 | 45 | — | 15 | 270.7 |
| 20 | 10 | 55 | — | 15 | 267.7 |
| 26.67 | 13.33 | 45 | — | 15 | 269.2 |
| 12.35 | 17.84 | 18.47 | 33.85 | 17.49 | 273.5 |
| 9.61 | 13.88 | 7.83 | 52.68 | 16 | 275.0 |
| 7.74 | 11.17 | — | 66.24 | 14.85 | 275.9 |

| % NC | % NFENG | % APC | % NFBN | % AL | % HMX | ISE |
|---|---|---|---|---|---|---|
| 10 | 40 | 30 | — | 20 | — | 271.3 |
| 15 | 30 | 34 | — | 21 | — | 268.0 |
| 20 | 40 | 23 | — | 17 | — | 271.5 |
| 10 | 10 | 12 | 10 | 13.3 | 44.7 | 274.8 |
| 10 | 15 | 21.3 | 15 | 12.5 | 26.2 | 274.1 |
| 15 | 15 | 19.1 | 15 | 12.4 | 23.5 | 272.8 |
| 15 | 20 | 24.3 | 20 | 10.7 | 10.0 | 272.3 |

NOTE:
NFPA    2,3-bis-Difluoraminopropyl Acrylate
NFENG    3-((1,2-bis-Difluoramino)ethoxy)-1,2-Propanedinitrate
APC    Ammonium perchlorate
HMX    Cyclotetramethylene tetranitramine
AL    Aluminum
NC    Nitrocellulose
NFBN    3,4-bis-Difluoraminobutyronitrile
ISE    Calculated specific impulse The following nitration experiment is typical: (The detailed preparation of a typical precursor is also given):

EXAMPLE I

Reaction of tetrafluorohydrazine with 2-Methyl-4-vinoxymethyl-1,3-Dioxolane

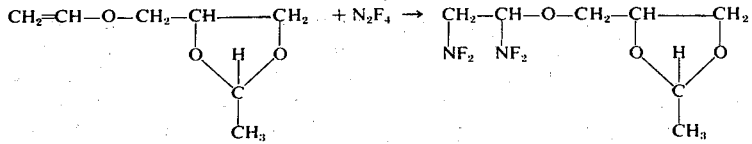

To a glass Aerosol tube of 100 ml. capacity was introduced 8.6 grams (0.05 mole) 2-methyl-4-vinoxymethyl-1,3-dioxolane and 30 ml. of carbon tetrachloride. The tube was then placed in position on a high pressure manifold, degassed thoroughly under vacuum then flushed and degassed three times with nitrogen. Tetrafluorohydrazine was then introduced into the reactor tube to give an initial pressure of 83 psi. An initial pressure drop was due to absorption of tetrafluorohydrazine in solvent. After recharging to 83 psi. with tetrafluorohydrazine, the mixture was heated to 80° C. During the next three hours, the tetrafluorohydrazine pressure was maintained between 83–39 psi. by recharging the system at frequent intervals. The total number of recharges was ten. The heating bath was lowered and after cooling the excess tetrafluorohydrazine was vented to the air. The reactor was then flushed with nitrogen and degassed three times, after which air was introduced into the reactor and it was allowed to stand for a period of fifteen minutes. The Aerosol tube with contents was then removed from the manifold poured into a 100 ml. flask and the solvent removed on a rotary stripper at reduced pressure. The residue obtained weighed 13.7 grams (99%) and identified as 2-methyl-4-(1,2-bis-difluoraminoethoxymethyl)-1,3-dioxolane by its infrared spectrum and elemental analysis.

Analysis: Calculated for $C_7H_{12}F_4N_2O_3$: % C, 33.85; % H, 4.84; % F, 30.65; % N, 11.28; Found: % C, 35.09; % H, 5.16; % F, 29.70; % N, 11.17.

Hydrolysis of
2-Methyl-4-(1,2-bis-Difluoraminoethoxymethyl)-1,3-Dioxolane

To a 300 ml. flask fitted with magnetic stirrer containing 90 ml. water, 10 ml. concentrated hydrochloric acid and 100 ml. methanol was added 13.8 grams (0.05 mole) 2-methyl-4-(1,2-bis-difluoraminoethoxymethyl)-1,3-dioxolane. The mixture was stirred at ambient temperature for a period of twenty-four hours. After removal of the methanol at reduced pressure, the aqueous solution was extracted with three 100 ml. portions of ether. The ether extracts were combined, washed once with water and dried over anhydrous magnesium sulfate. The ether was removed at reduced pressure to yield 9.65 grams (87%) of a clear viscous residue identified by its infrared spectrum and elemental analysis as 3-((1,2-bis-difluoramino)ethoxy)-1,2-propanediol. Characterization was carried out on the crude diol.

Analysis: Calculated for $C_5H_{10}F_4N_2O_3$: % C, 27.03; % H, 4.50; % F, 34.24; % N, 12.63; Found: % C, 28.99; % H, 4.98; % F, 32.10; % N, 13.36.

Nitration of
3-((1,2-bisdifluoramino)ethoxy)-1,2-Propanediol

The following nitration experiment is typical: To a 50 ml. 3-necked flask equipped with a water condenser (with drying tube), dropping funnel, magnetic stirrer and air sparging tube was placed 5.9 ml. (0.125 moles) of 90% fuming nitric acid. The acid was air sparged until it became clear (approximately 15 minutes). The air sparging tube was then replaced with a thermometer, an ice-water bath placed around the flask, and with good stirring 6.9 ml. (0.125 moles) of 96% sulfuric acid was slowly added via the dropping funnel. Then 5.6 grams (0.015 moles) of 3-((1,2-bisdifluoramino)ethoxy)-1,2-propanediol, diluted with 25 ml. of methylene chloride was slowly added (exothermic reaction) to the mixed acid solution. The temperature was maintained at 15° to 20° C. by means of a chilled water bath during the addition of the diol and then raised to reflux temperature of methylene chloride (39° to 40° C.). The solution was allowed to reflux for forty-five minutes, cooled, and transferred to a separatory funnel with a few milliliters of methylene chloride. The acid layer was separated and the methylene chloride layer washed with cold water, twice with cold saturated sodium carbonate, again with cold water, and then dried over 4 to 5 grams of anhydrous magnesium sulfate. After five or ten minutes, the solution was filtered and the methylene chloride removed by means of a rotary evaporator. The product, 3-((1,2-bisdifluoramino)ethoxy)-1,2-propanedinitrate, was a viscous slightly yellow colored material that was not distilled. A total of 7.7 grams (99%) of the dinitrate was obtained, $N_D^{20}$ 1.4414, sensitivity (Picatinny Impact Tester) 22.8 in. (50% Fire Level).

Analysis: Calculated for $C_5H_8F_4N_4O_7$: % C, 19.24; % H, 2.58; % N, 17.95. Found: % C, 22.10; % H, 3.07; % N, 17.88.

I claim:

1. Compounds of the general formula

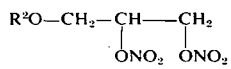

in which $R^2$ is selected from the group consisting of

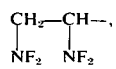

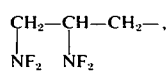

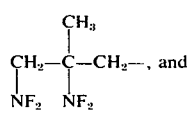

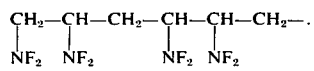

2. A compound of the formula

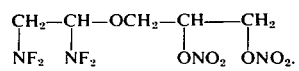

3. A compound of formula

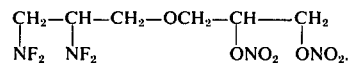

4. A compound of the formula

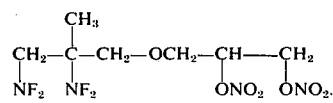

5. A compound of the formula

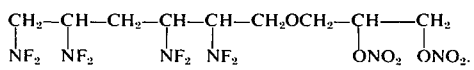

6. A process for the preparation of compounds of the general formula

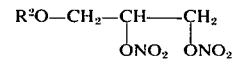

in which $R^2$ is as defined in claim 1, which comprises nitrating, with a mixture of sulfuric and nitric acids, diols of the general formula

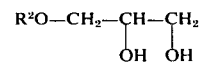

in which $R^2$ is as defined in claim 1.

7. The process as set forth in claim 6 in which the temperature of the reaction mixture is maintained at 10° to 25° C.

8. The process as set forth in claim 6 in which the diol is dissolved in an inert organic solvent, said inert solvent being non-reactive with the reactants or the resulting product.

9. The process as set forth in claim 6 in which the sulfuric and nitric acids are present in equimolar amounts.

10. The process as set forth in claim 8 in which the inert organic solvent is methylene chloride.

* * * * *